United States Patent [19]

Stickley et al.

[11] Patent Number: 5,952,537
[45] Date of Patent: Sep. 14, 1999

[54] PREPARATION OF CYCLOALKYLACETYLENE COMPOUNDS USING DIALKYLAMINOMAGNESIUM HALIDE OR BIS(DIALKYLAMINO) MAGNESIUM

[75] Inventors: Kurt R. Stickley, Gahanna; David B. Wiley, Warsaw, both of Ohio

[73] Assignee: Wiley Organics, Inc., Coshocton, Ohio

[21] Appl. No.: 09/042,409

[22] Filed: Mar. 13, 1998

[51] Int. Cl.[6] .............................. C07C 2/00; C07C 1/20; C07C 1/207; C07C 13/00
[52] U.S. Cl. ..................... 585/534; 585/20; 585/359; 585/358; 585/365; 585/407; 585/408
[58] Field of Search ...................... 585/534, 359, 585/20, 358, 365, 407, 408

[56] References Cited

U.S. PATENT DOCUMENTS

| | | | |
|---|---|---|---|
| 4,263,217 | 4/1981 | Malpass et al. | 556/175 |
| 4,595,779 | 6/1986 | Morrison et al. | 564/2 |
| 5,002,689 | 3/1991 | Mehta et al. | 252/182.12 |
| 5,519,021 | 5/1996 | Young et al. | 514/230.5 |
| 5,663,467 | 9/1997 | Thompson et al. | 585/359 |

OTHER PUBLICATIONS

Gary S. Silverman, Handbook of Grignard Reagents, *Marcel Dekker, Inc.*, 1996, pp. 450–453.

Basil J. Wakefield, Organomagnesium Methods in Organic Synthesis, *Academic Press*, 1995, pp. 186–191.

Chemical Abstracts, 28–Heterocyclic Compounds (More Than One Hetero Atom), vol. 125, No. 17, 1996, p. 1107.

Kazuhiro Kabayashi, et al., *Bull. Chem. Soc. Jpn.*, Reactions of Sulfoxides with Magnesium Amides. Transformation of Sulfoxides into Sulfides, Dithioacetals, and Vinyl Sulfides, 1995, pp. 1401–1407.

Andrew S. Thompson, et al., Use of an Ephedrine Alkoxide to Mediate Enantioselective Addition of an Acetylide to a Prochiral Ketone: Asymmetric Synthesis of the Reverse Transcriptase Inhibitor L–743, 726, *Tetrahedron Letters*, vol. 36, No. 49, 1995, pp. 8937–8940.

*Primary Examiner*—Glenn Caldarola
*Assistant Examiner*—In Suk Bullock
*Attorney, Agent, or Firm*—Thompson Hine & Flory LLP

[57] ABSTRACT

The process of invention reacts an alkynyl halide with a mixture that includes a dialkylaminomagnesium halide or a bis(dialkylamino)magnesium compound to produce a cycloalkylacetylene compound. Preferably, the dialkylaminomagnesium halide compound is of the general formula $R_2NMgX$ (where R is a linear, branched, or cyclic alkyl substituent or $R_2N$ represents a heterocyclic alkyl amine and X is Cl, Br, or I) and the bis(dialkylamino)magnesium compound is of the general formula $(R_2N)_2Mg$ (where R is a linear, branched, or cyclic alkyl substituent or $R_2N$ represents a heterocyclic alkylamine). In a preferred method of the invention, the reaction is conducted at moderate temperatures for a period of about 12 to 24 hours. The reaction mixture preferably includes tetrahydrofuran (THF), or a hydrocarbon, or a hydrocarbonether mixture. The preferred compounds produced by this process are cycloalkylacetylene compounds having 5 to 20 carbons, such as cyclopropylacetylene and cyclobutylacetylene.

13 Claims, No Drawings

PREPARATION OF CYCLOALKYLACETYLENE COMPOUNDS USING DIALKYLAMINOMAGNESIUM HALIDE OR BIS(DIALKYLAMINO) MAGNESIUM

The invention relates generally to a novel method of preparing cycloalkylacetylenes. More specifically, the invention concerns the synthesis of cycloalkyacetylenes by reacting an alkynyl halide with a dialkylaminomagnesium halide compound such as diisopropylaminomagnesium chloride or a bis(dialkylamino)magnesium compound, such as bis(diisopropylamino)magnesium.

Cycloalkylacetylenes (CAA's) such as ethynylcyclopropane (cyclopropylacetylene) have previously been synthesized by reacting 2.4 equivalents of n-butyllithium (n-BuLi) in tetrahydrofuran (THF) with one equivalent of 5-chloropentyne. The yield of ethynylcyclopropane obtained by this method is temperature dependent, with lower temperatures resulting in higher yields due to less intermolecular head-to-tail coupling of the reaction intermediates. Yields range from 60% to 80% when the reaction is conducted at temperatures from 5° C. to –40° C., respectively.

Although n-BuLi is frequently used to carry out the aforementioned reaction, it is both expensive and pyrophoric. Thus, n-BuLi is not an ideal reagent because its use increases costs of production and presents significant safety hazards for users unfamiliar with the handling of pyrophoric materials.

In an effort to overcome the shortcomings associated with the use of n-BuLi, reactions have also been carried out using lithium diisopropylamide (LDA). LDA possesses a number of advantages over n-BuLi as a reagent in the aforementioned reactions. LDA is commercially available as a non-pyrophoric solution. It has also been found that when the aforementioned reaction is conducted with LDA in place of n-BuLi, a yield of 80% ethynylcyclopropane could be obtained at a temperature of 0° C., while the method utilizing n-BuLi as a reagent required a temperature of –40° C. to achieve such a yield.

Although LDA does obviate some of the problems associated with the use of n-BuLi, it still possesses a number of shortcomings. For example, stable and non-pyrophoric formations of LDA are relatively expensive. Furthermore, the reaction temperature must be maintained below 5° C. because tetrahydrofuran, the preferred solvent medium, is not stable in the presence of LDA at higher temperatures.

Accordingly, a need exists for a method of preparing cycloalkylacetylene compositions that gives good yields (e.g., in excess of 80%) at ambient temperatures or above, uses readily-available and inexpensive materials, requires standard laboratory or processing equipment, can be completed in a substantially short period of time (e.g. cycle times <24 hours), and which utilizes materials that do not present potentially grave safety hazards for the user (e.g., are not pyrophoric).

SUMMARY OF THE INVENTION

The process of the invention provides cycloalkylacetylene compounds having 5 to 20 carbons. Broadly, the process reacts an alkynyl halide with a dialkylaminomagnesium halide compound of the form $R_2NMgX$ or a bis (dialkylamino)magnesium compound of the form $(R_2N)_2Mg$ to produce the desired cycloalkyacetylene compound.

The compounds produced by this process are cycloalkylacetylene compounds having the formula $ZCHC_2H$ where Z is a divalent alkylene bridge of the formula $—(CH_2)_n—$ and n is equal to 2 to 17 units. These compounds are produced by the cyclization of alkynyl halides having the general formula $X(CH_2)_nC_2H$ where n is equal to 3 to 18 units and X is Cl, Br, or I. The process is especially useful to produce cyclopropylacetylene.

The process can be carried out in an ether, (e.g., tetrahydrofuran (THF), dibutyl ether, etc.) an ether/hydrocarbon mixture, or a hydrocarbon medium where the hydrocarbons can be either aromatic (e.g., benzene, toluene, xylene, etc.) or linear or branched alkanes (e.g., Isopar C, Isopar G, Isopar H, etc.). The preferred solvent is tetrahydrofuran (THF). It has been determined experimentally that THF is stable to dialkylaminomagnesium halides and bis (dialkylamino)magnesium compounds for hours at reflux (64° C.). Depending on the specific CAA being formed, a higher boiling medium may be preferred in order to speed up the cyclization process or to aid in the isolation of the product. Thus, the choice of other solvents or solvent mixtures may prove more desirable. The process can be carried out at temperatures as low as –5° C. and is typically limited by the stability of the dialkylaminomagnesium halides/bis(dialkylamino)magnesium compounds and the amount of dehydrohalogenated by-products which can form at elevated temperatures. For example, the preparation of cyclopropylacetylene requires a reaction temperature of less than 40° C. in order to minimize the amount of dehydrohalogenated by-products.

The $R_2NMgX$ compounds are readily obtained by reacting a dialkylamine ($R_2NH$ where R is a branched, linear, or cyclic alkyl substituent having 1 to 6 carbon atoms or where the R substituents combine to form a heterocyclic alkyl amine having 3 to 6 carbon atoms) with a Grignard (R'MgX where R' is a 1°, 2° or 3° alkyl substituent and X is Cl, Br, or I) at ambient or slightly elevated temperatures (<64° C.). For the present, the structures of the dialkylaminomagnesium halides are given on the assumption of metathesis reactions. No consideration of complexation, aggregation, or other complication is included.

The bis(dialkylamino)magnesium compounds $(R_2N)_2Mg$ are readily obtained by reacting the dialkylaminomagnesium halide with the desired lithium amide ($R_2NLi$ where R is a branched, linear, or cyclic alkyl substituent having 1 to 6 carbon atoms or where the R substituents combine to form a heterocyclic alkyl amine having 3 to 6 carbon atoms). Alternatively, the bis(dialkylamino)magnesium compounds can also be prepared by refluxing the appropriate dialkylamine ($R_2NH$ where R is defined as above) with a dialkylmagnesium compound (e.g., with dibutylmagnesium) in an ether, or ether/hydrocarbon mixture, or a hydrocarbon medium where the hydrocarbons can be either aromatic (e.g., benzene, toluene, xylene, etc.) or linear or branched alkanes (e.g., Isopar C, Isopar G, Isopar H, etc.). The bis(dialkylamino)magnesium compounds differ from the dialkylaminomagnesium halides in that they are more soluble in hydrocarbon solvents and are stronger bases. For the present, the structures of the bis(dialkylamino) magnesium compounds are given on the assumption of metathesis reactions. No consideration of complexation, aggregation, or other complication is included.

The preferred dialkylaminomagnesium halides for use in the present invention include diisopropylaminomagnesium bromide (DAMB), diisopropylaminomagnesium chloride (DAMC), 2,2,6,6-tetramethylpiperidinomagnesium bromide (TMPMB), and 2,2,6,6-tetramethylpiperidinomagnesium chloride (TMPMC). Preferred bis(dialkylamino)magnesium compounds for use in the present invention include bis(2,2,6,6- tetramethylpiperidino)magnesium (BTMPM) and bis(diisopropylamino)magnesium (BDAM).

DETAILED DESCRIPTION OF THE INVENTION

The present invention will be understood more fully from the description which follows, and from the accompanying examples, in which particular embodiments of the process of the invention are shown. It is understood at the outset, however, that persons of skill in the appropriate arts may modify the invention herein described while still achieving the favorable results thereof. Accordingly, the description and examples which follow are to be understood as being a broad teaching disclosure directed to persons of skill in the appropriate arts, and are not to be understood as limiting upon the present invention. The scope of the invention is to be determined by the appending claims.

The process is initiated by reacting a secondary amine ($R_2NH$ as previously defined) with an alkylmagnesium halide (i.e. a Grignard reagent of the form R' MgX where R' is typically a primary, secondary to tertiary alkyl group) to produce a reaction mixture containing the dialkylaminomagnesium halide compound of the form $R_2NMgX$. The alkynyl halide is then added to the reaction mixture. Generally, the reaction is conducted at ambient temperatures (e.g., 20 to 30° C.) or above for a period of about 12 to 24 hours. The reaction mixture is preferably carried out in an ethereal solvent such as tetrahydrofuran (THF), or a hydrocarbon/ether mixture where the hydrocarbons can be either aromatic (i.e. benzene, toluene, xylene, etc.) or linear or branched alkanes (i.e. Isopar C, Isopar G, Isopar H, etc.).

The process of the invention is preferably initiated by reacting an excess of alkylmagnesium halide (i.e. a Grignard reagent such as ethylmagnesium bromide) with the secondary amine (e.g., diisopropylamine (DIPA)) in THF to form a reaction mixture containing a dialkylaminomagnesium halide (e.g., diisopropylaminomagnesium bromide (DAMB)). The amine is typically present in the reaction mixture when the Grignard is formed. Thus, the diisopropylamine reacts with the ethylmagnesium bromide as it is produced in situ to form the DAMB according to Equation (1):

(1)

i-Pr\
    NH + C$_2$H$_5$MgBr(ex) →$^{THF}$ i-Pr\NMgBr + C$_2$H$_6$↑
i-Pr/                                          i-Pr/

The 5-chloropentyne is then added to the reaction mixture, where it is cyclized:

(2)

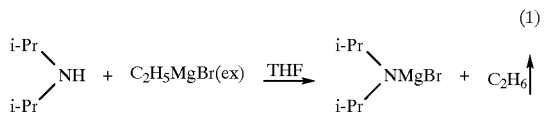

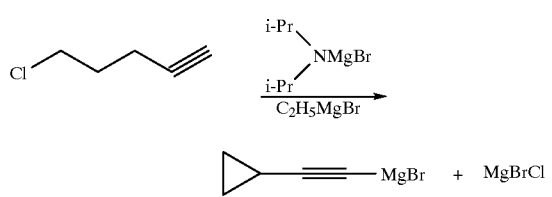

Advantageously, the amount of secondary amine (i.e., DIPA) used to produce the reaction mixture can be less than one stoichiometric equivalent because the dialkylaminomagnesium halide of the form $R_2NMgx$ is regenerated after the cyclization reaction by reaction of the amine released according to equation (2) with the excess alkylmagnesium halide present in solution. The amount of the amine realtive to the alkynyl halide can range from a catalytic amount to a stoichiometric amount, but the reaction proceeds smoothly with less than a stoichiometric amount, e.g., about 50% of a stoichiometric amount is typically used. The metalated cyclic acetylene produced by this process is readily released via a dilute acid or water quench, as is customary when performing Grignard reactions.

(3)

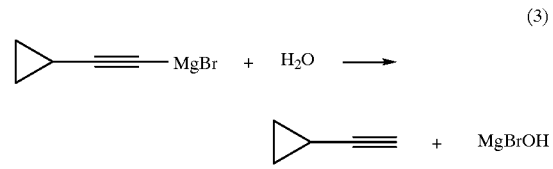

The molar ratio of alkyl Grignard to alkyne preferably exceeds the stoichiometric amount of 2:1 and is typically about 2.4:1. Using a 20% excess of alkyl Grignard in the reaction insures complete consumption of the alkyne and allows for a less than theoretical yield of the alkyl Grignard. Our results have shown that one byproduct in the Grignard formation is a tertiary amine. This tertiary amine presumably arises from the reaction of the dialkylaminomagnesium halide formed in situ with the unreacted alkyl halide present in the Grignard. This tertiary amine is not detrimental to the follow on chemistry.

When using THF as a solvent, the molar ratio of alkyne to the dialkylaminomagnesium halide is typically 2 to 1 respectively. If more dialkylaminomagnesium halide is used, the reaction mixture becomes very thick due to the low solubility of the dialkylaminomagnesium halide. If less dialkylaminomagnesium halide is used, the reaction times become extended due to the fact that there is a reduced amount of the cyclizing reagent (i.e. dialkylaminomagnesium halide) present in solution. Based upon these considerations the molar ratio could be higher than 2 to 1 such as up to 3 to 1.

The same process can be used to prepare other CAA's such as cyclobutylacetylene by cyclizing 6-chlorohexyne, Equation (4):

(4)

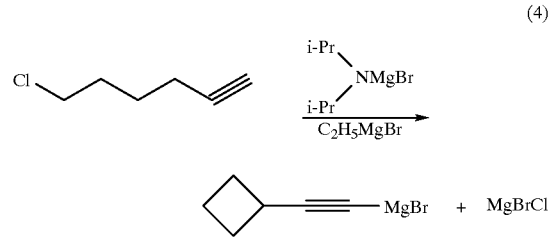

The process of the invention can also be initiated by reacting dibutylmagnesium (Bu)$_2$Mg (1.0 M in heptanes) with a secondary amine (e.g. diisopropylamine (DIPA)) in THF at reflux to form a reaction mixture containing a bis(dialkylamino)magnesium (e.g., bis(diisopropylamino) magnesium (BDAM)). Equation (5). The bis(dialkylamino) magnesium has been shown to be stable toward THF at these temperatures.

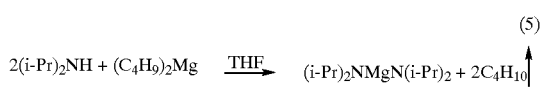

(5)

The 5-chloropentyne is then added to the mixture where it is cyclized.

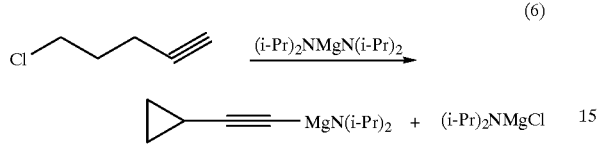

(6)

Advantageously, the amount of the bis(dialkylamino)magnesium used to produce the reaction mixture can be less than two stoichiometric equivalents because the byproduct from the cyclization reaction is a dialkylaminomagnesium halide which can in turn react with the metallated 5-chloropentyne. Equation (7).

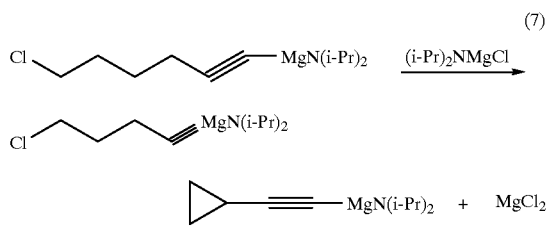

(7)

The ratio of bis(dialkylamino)magnesium to alkyne is typically about 1.7 to 1 respectively. As in the case of the dialkylamino halide, the amount of the bis(dialkylamino)magnesium is a function of solubility and reaction time considerations.

The metalated cyclic acetylene produced by this process is readily released via a dilute acid or water quench, as is customary when performing Grignard reactions. Equation (8).

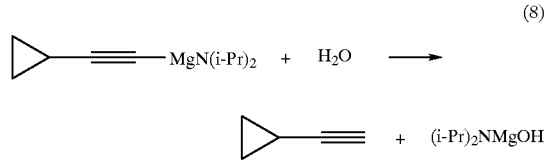

(8)

The same process can be used to prepare cyclobutylacetylene by cyclizing 6-chlorohexyne, Equation (9):

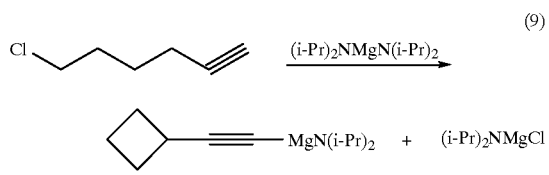

(9)

The invention is further explained by the following illustrative Examples:

EXAMPLE I

Preparation of diisopropylaminomagnesium bromide (DAMB)

Into a 1 liter round bottom flask equipped with an addition funnel and a reflux condenser were placed magnesium turnings (24.3 g, 1.0 mol), diisopropylamine (20.2 g, 0.2 mol) and THF (500 ml). Bromoethane (120.0 g, 1.1 mol) was added dropwise to this mixture via the addition funnel at such a rate as to maintain a refluxing solution. Ethane was evolved during the addition. The reaction was determined to be complete once all of the magnesium was consumed. This process produced a solution containing EtMgBr and DAMB.

EXAMPLE II

Preparation of diisopropylaminomagnesium chloride (DAMC)

Preparation of DAMC was performed in a manner similar to that of Example I, except that this process employed chloroethane in place of bromoethane. This reaction produced a solution containing EtMgCl and DAMC.

EXAMPLE III

Cyclization of 5-chloropentyne to cyclopropylacetylene with DAMB

5-Chloropentyne (41.0 g, 0.4 mol) was added dropwise to the reaction mixture (containing EtMgBr and DAMB) of Example I at such a rate as to not exceed a reaction temperature of 30° C. After the addition was complete, the reaction mixture was allowed to stir for an additional 18 hours (<30° C.) in order to complete the cyclization. Upon completion the mixture was quenched with dilute acid (0.5 N HCl) in order to release the desired product. The crude reaction mixture was subjected to GC-FID analysis, which showed a yield of >95% of cyclopropylacetylene.

EXAMPLE IV

Cyclization of 6-chlorohexyne to cyclobutylacetylene with DAMB

Preparation of cyclobutylacetylene was performed in a similar manner to that of Example III, except that 6-chlorohexyne rather than 5-chloropentyne was added to the reaction mixture of Example I and solvent reflux was required in order to afford the cyclization. The reaction mixture was quenched with dilute acid and subjected to GC-FID analysis, which showed a yield of >90% of cyclobutylacetylene.

EXAMPLE V (Comparison)

Reaction performed without dialkylaminomagnesium halide compound

The cyclization process was performed in a manner similar to that of Example III, except that 5-chloropentyne was added to EtMgBr in THF, but with no dialkylaminomagnesium halide compound present (e.g., DAMB or its precursor DIPA). The reaction mixture was quenched with dilute acid and subjected to GC-FID analysis, which showed no detectable trace of cyclopropylacetylene. Thus, in the absence of the dialkylaminomagnesium halide compound, cyclization does not occur.

EXAMPLE VI

Cyclization of 5-chloropentyne to cyclopropylacetylene with DAMC

5-Chloropentyne (41.0 g, 0.4 mol) was added to the reaction mixture (containing EtMgCl and DAMC) of Example II at such a rate as to maintain the reaction temperature below 30° C. The reaction mixture was allowed to stir for an additional 10 hours while maintaining a reaction temperature below 30° C. in order to complete the cyclization. The reaction mixture was quenched with dilute acid to release the product and subjected to GC-FID analysis, which showed a yield of >95% of cyclopropylacetylene.

EXAMPLE VII

Cyclization of 6-chlorohexyne to cyclobutylacetylene with DAMC

Preparation of cyclobutylacetylene was performed in a similar manner to that of Example VI, except that 6-chlorohexyne instead of 5-chloropentyne was added to the reaction mixture of Example II. Because the reaction was slow, solvent reflux (64° C.) was used to afford the cyclization. The reaction mixture was quenched with dilute acid and subjected to GC-FID analysis which showed a yield of >90% of cyclobutylacetylene.

EXAMPLE VIII

Cyclization of 5-chloropentyne to cyclopropylacetylene with TMPMB

Preparation of cyclopropylacetylene is performed in a manner similar to that of Example III, except that 5-chloropentyne is added to a reaction mixture containing EtMgBr and TMPMB instead of the reaction mixture of Example I. The reaction mixture was quenched with dilute acid and subjected to GC-FID analysis, which showed a yield of >90% of cyclopropylacetylene.

EXAMPLE X

Cyclization of 5-chloropentyne to cyclopropylacetylene with BTMPM

In a 100 mL round bottom flask equipped with a reflux condenser was placed dibutylmagnesium (3.46 g, 0.025 mol, 25 mL, 1.0 M in heptanes), THF (25 mL), and 2,2,6,6-tetramethylpiperidine (7.05 g, 0.05 mol). This mixture was then heated to reflux for 3 hours to form bis(tetramethylpiperidino)magnesium. This mixture was then cooled to 30° C. and 5-chloropentyne (1.506 g, 0.0147 mol) was added dropwise over a five minute period. The resulting mixture was then allowed to stir for an additional 1 hour. The reaction mixture was quenched with dilute acid and subjected to GC-FID analysis, which showed a yield of >90% of cyclopropylacetylene.

EXAMPLE XI

Cyclization of 6-chlorohexyne to cyclobutylacetylene with BTMPM

Preparation of cyclobutylacetylene is performed in a manner similar to that of Example X, except that 6-chlorohexyne is used in place of the 5-chloropentyne and the reaction mixture was heated to reflux for 18 hours to afford the cyclization. The reaction mixture was quenched with dilute acid and subjected to GC-FID analysis, which showed a yield of >70% of cyclobutylacetylene.

EXAMPLE XII

Cyclization of 5-chloropentyne to cyclopropylacetylene with BDAM

Preparation of cyclopropylacetylene is performed in a manner similar to that of Example X, except that diisopropylamine was used in place of 2,2,6,6-tetramethylpiperidine. The reaction mixture was quenched with dilute acid and subjected to GC-FID analysis, which showed a yield of >90% of cyclopropylacetylene.

EXAMPLE XIII

Cyclization of 6-chlorohexyne to cyclobutylacetylene with BDAM

Preparation of cyclobutylacetylene was performed in a manner similar to that of Example XI, except that diisopropylamine was added to a reaction mixture instead of the 2,2,6,6-tetramethylpiperdine. The reaction mixture was quenched with dilute acid and subjected to GC-FID analysis, which showed a yield of >70% of cyclobutylacetylene.

Having described the invention in detail it will be apparent that numerous modifications and variations are possible without departing from the spirit and scope of the following claims.

What is claimed is:

1. A process of preparing cycloalkylacetylene compounds which comprises adding an alkynyl halide to a reaction mixture containing a dialkylaminomagnesium halide or a bis(dialkylamino)magnesium to effect cyclization of the alkynyl halide and formation of a cycloalkylacetylene compound.

2. A process according to claim 1 wherein the reaction mixture further includes an ethereal solvent, an ether/hydrocarbon mixture, or a hydrocarbon solvent where the hydrocarbons can be either aromatic or linear or branched alkanes.

3. The process according to claim 1 wherein the cyclization is effected at temperatures ranging from about −5° C. or higher.

4. The process according to claim 1 wherein the reaction mixture contains a dialkylaminomagnesium halide of the formula $R_2NMgX$ where R is a linear, branched, or cyclic alkyl substituent or the R groups combine to form a heterocyclic alkylamine, and X is Cl, Br, or I.

5. The process according to claim 1 wherein the reaction mixture contains a bis(dialkylamino)magnesium of the formula $(R_2N)_2Mg$ where R is a linear, branched, or cyclic alkyl substituent or the R groups combine to form a heterocyclic alkylamine.

6. The process according to claim 1 where in the alkynyl halide is a compound of the general formula $X(CH_2)_nC_2H$ where n is equal to 3 to 18 units and X is Cl, Br, or I.

7. The process according to claim 1 wherein the cycloalkylacetylene compound is a compound of the general formula $Z\,CHC_2H$ where Z is a divalent alkylene group of the formula $—(CH_2)_n—$ and n is equal to 2 to 17 units.

8. The process of claim 1 wherein the reaction medium is prepared by reacting a secondary alkylamine with a Grignard reagent resulting in a reaction medium containing dialkylaminomagnesium halide.

9. The process of claim 8 wherein said secondary alkylamine has the formula $R_2NH$ where R is a straight chain, branched chain or cyclic alkyl group or said R groups combine to form an alkylene bridge and the Grignard reagent is a compound of the formula R'MgX where R' is a primary, secondary or tertiary alkyl group and X is Cl, Br, or I.

10. The process of claim 1 wherein the reaction medium is prepared by reacting a secondary alkylamine with a dialkylmagnesium compound and the reaction mixture contains bis(dialkylamino)magnesium.

11. The process of claim 10 wherein secondary alkylamine has the formula $R_2NH$ where R is a straight chain, branched chain or cyclic alkyl group or said R groups combine to form an alkylene bridge and the dialkylmagnesium is dibutylmagnesium.

12. The process of claim 1 wherein said secondary alkylamine is reacted in less than a stoichrometric amount.

13. The process of claim 1 wherein said bis(dialkylamino) magnesium reagent is reacted in less than a stoichiometric amount.

* * * * *